(12) United States Patent
Bian et al.

(10) Patent No.: US 10,973,823 B2
(45) Date of Patent: Apr. 13, 2021

(54) ANTI-CANCER COMPOSITION CONSISTING OF HALOFUGINONE AND SESQUITERPENE LACTONE COMPOUNDS OF ARTEMISIA APIACEA AND USE THEREOF

(71) Applicant: Hong Kong Baptist University, Hong Kong (CN)

(72) Inventors: Zhaoxiang Bian, Hong Kong (CN); Guoqing Chen, Hong Kong (CN); Ruihong Gong, Hong Kong (CN); Dajian Yang, Chongqing (CN); Aiping Lyu, Hong Kong (CN)

(73) Assignee: Hong Kong Baptist University, Hong Kong (CN)

( * ) Notice: Subject to any disclaimer, the term of this patent is extended or adjusted under 35 U.S.C. 154(b) by 174 days.

(21) Appl. No.: 16/067,839

(22) PCT Filed: Sep. 27, 2016

(86) PCT No.: PCT/CN2016/100329
§ 371 (c)(1),
(2) Date: Oct. 19, 2018

(87) PCT Pub. No.: WO2017/118114
PCT Pub. Date: Jul. 13, 2017

(65) Prior Publication Data
US 2019/0388424 A1    Dec. 26, 2019

(30) Foreign Application Priority Data
Jan. 5, 2016 (CN) .......................... 201610006000.1

(51) Int. Cl.
*A61K 31/517* (2006.01)
*A61P 35/00* (2006.01)
*A61K 31/366* (2006.01)

(52) U.S. Cl.
CPC .......... *A61K 31/517* (2013.01); *A61K 31/366* (2013.01); *A61P 35/00* (2018.01)

(58) Field of Classification Search
CPC .............................. A61K 31/517; A61P 35/00
USPC .................................................... 514/266.22
See application file for complete search history.

(56) References Cited

U.S. PATENT DOCUMENTS 6,028,075 A * 2/2000 Pines ...................... A61P 35/00
514/266.22

OTHER PUBLICATIONS

Buommino et al., "Artemisinin reduces human melanoma cell migration by down-regulating aVβ3 integrin and reducing metalloproteinase 2 production", Investigational New Drugs, vol. 27, No. 5, pp. 412-418 (2009).*

Huang, Boxian. "Control of Chicken Coccidiosis and Prescription Drug Screening" Agriculture, China Master's Theses Full-Text Database, No. 5, May 15, 2011 (May 15, 2011), D050-167, particularly pp. 19 and 28.

* cited by examiner

*Primary Examiner* — Kevin E Weddington
(74) *Attorney, Agent, or Firm* — Spruson & Ferguson (Hong Kong) Limited

(57) ABSTRACT

Provided is a combined pharmaceutical composition of HF and an *Artemisia annua* sesquiterpene lactone compound for treating cancers. The active ingredients of the combined pharmaceutical composition consist of HF and an *Artemisia annua* sesquiterpene lactone compound. HF and ATS have significant synergistic effect. The activity of the combined pharmaceutical of HF and ATS is comparable or even higher than that of the anti-cancer drug 5-FU.

6 Claims, 2 Drawing Sheets

ANTI-CANCER COMPOSITION CONSISTING OF HALOFUGINONE AND SESQUITERPENE LACTONE COMPOUNDS OF ARTEMISIA APIACEA AND USE THEREOF

FIELD OF THE INVENTION

The present disclosure generally relates to an anti-cancer combined pharmaceutical, and in particular, to an anti-cancer composition comprising halofuginone and an *Artemisia annua* sesquiterpene lactone compound and the application thereof.

BACKGROUND OF THE INVENTION

Halofuginone (HF) is a type of alkaloid, and is a derivative of the active ingredient of the Chinese herb, i.e. febrifugine. The molecular formula of HF is $C_{16}H_{17}BrClN_3O_3 \cdot HBr$, existing as white or light grey crystalline powder, with an odorless smell and a bitter taste. Studies on HF began from as early as 1975. HF has been used as a broad-spectrum anticoccidial drug for quite a long time. In recent years, with studies on HF going deeper and deeper, HF has been found to be able to promote wound healing and inhibit tissue fibrosis. HF has also been found to exhibit excellent performance in anti-tumor pre-clinical studies, showing significant inhibitory effect on many cancer models, such as liver cancer, sarcoma, brain cancer, bladder cancer, breast cancer and prostate cancer.

Artemisinin (ATS), dihydroartemisinin (DAT), artesunate (ASU), or artemether (ATM), etc. are sesquiterpene lactone pharmaceuticals and the compound thereof containing peroxy groups, which are extracted from the stem and leaf of the plant *Artemisia annua*. In recent years, studies have found that *Artemisia annua* sesquiterpene lactone pharmaceuticals and the compound thereof exhibit good anti-cancer activity. There are probably two application modes when specifically using sesquiterpene lactone pharmaceuticals and the compound thereof as anti-cancer drugs: one mode is the single use of sesquiterpene lactone pharmaceuticals and the compound thereof as an anti-tumor drug, and the other mode is the combined use of the sesquiterpene lactone pharmaceuticals and the compound thereof, serving as a sensitizer, with other anti-tumor therapeutic drugs.

SUMMARY OF THE INVENTION

To provide an anti-cancer combined pharmaceutical with low toxicity and good anti-cancer activity, the present disclosure provides an anti-cancer composition comprising halofuginone and an *Artemisia annua* sesquiterpene lactone compound. The active ingredients of the combined pharmaceutical consist of halofuginone and an *Artemisia annua* sesquiterpene lactone compound.

The *Artemisia annua* sesquiterpene lactone compounds are a derivative of ATS and all sesquiterpene lactones extracted from *Artemisia annua*.

The *Artemisia annua* sesquiterpene lactone is one of ATS, DAT, ASU, or ATM.

The most preferable embodiment is the combination of ATS and HF.

Use of the anti-cancer composition comprising halofuginone and an *Artemisia annua* sesquiterpene lactone compound for the manufacture of a medicament for treating cancer.

Use of the anti-cancer composition comprising halofuginone and an *Artemisia annua* sesquiterpene lactone compound for the manufacture of a medicament for treating colon cancer.

Use of the anti-cancer composition comprising halofuginone and an *Artemisia annua* sesquiterpene lactone compound for the manufacture of a medicament for treating breast cancer.

Use of the anti-cancer composition comprising halofuginone and an *Artemisia annua* sesquiterpene lactone compound for the manufacture of a medicament for treating liver cancer.

Use of the anti-cancer composition comprising halofuginone and an *Artemisia annua* sesquiterpene lactone compound for the manufacture of a medicament for treating gastric cancer.

Use of the anti-cancer composition comprising halofuginone and an *Artemisia annua* sesquiterpene lactone compound for the manufacture of a medicament for melanoma.

The beneficial effects of the present disclosure are: the combination of HF and an *Artemisia annua* sesquiterpene lactone compound, such as ATS, DAT, ASU, or ATM, etc., has significant synergistic effects, wherein the activity of the combination pharmaceutical of HF and ATS is comparable with, or even higher than that of the anti-cancer drug 5-Fluorouracil (5-FU).

DETAILED DESCRIPTION OF THE INVENTION

Figure 1:
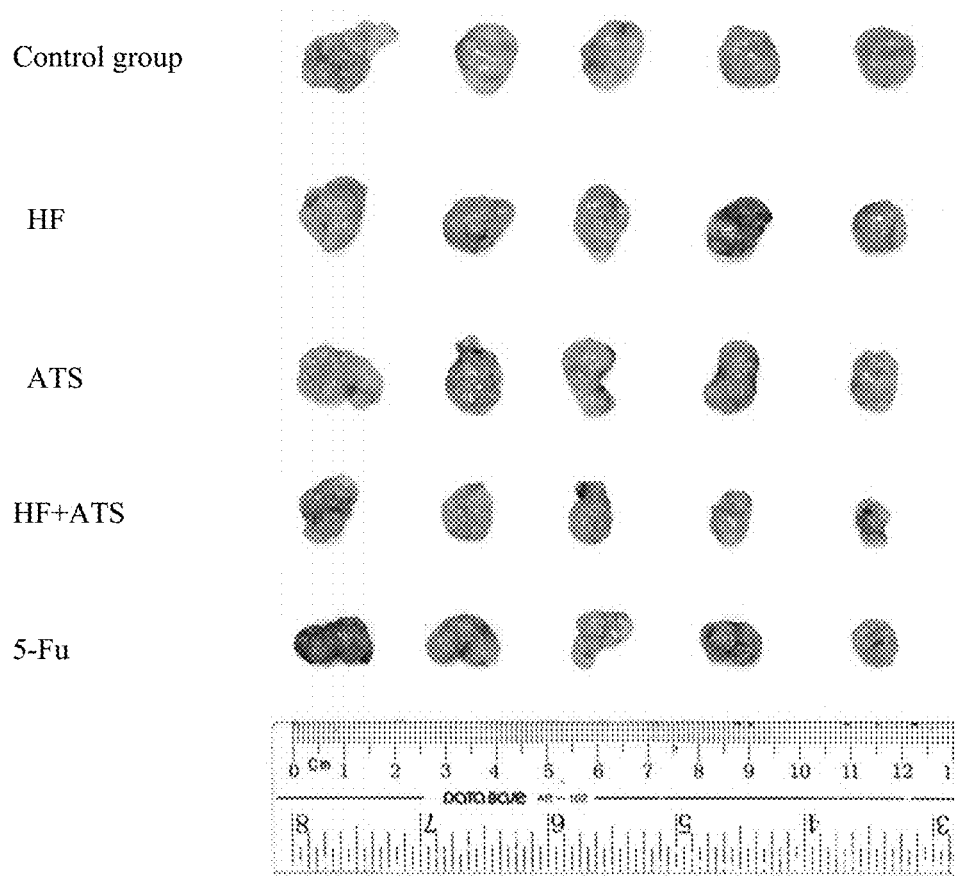
FIG. 1 illustrates the comparison of the volume of tumor tissues.

Embodiment 1: In Vitro Investigation on the Anti-Cancer Activity of the Combined Pharmaceutical of HF and ATS Human colon cancer cell line HCT-116 was seeded on a 96-well plate, with 100 μl of cell suspension in each well. The culture medium was DMEM supplemented with 10% FBS and 2 mM glutamate. 24 hours after cell seeding, the 96-well plate was added with HF, ATS, DAT, ASU, ATM, the combination of HF and ATS, the combination of HF and DAT, the combination of HF and ATM, the combination of HF and ASU, respectively, and the culture medium in the control group was not added with any drug. 24 hours after adding the compound, the cell survival rate was assessed using the MTT assay, and the combination index (CI) of the combined pharmaceutical of HF and ATS was calculated using the Calcusyn software. The results are shown in Table 1.

Tumor cell survival rate=the OD value of the experimental group/the OD value of the control group×100%

TABLE 1

The inhibitory effect of the combined pharmaceutical of HF and ATS on colon cancer cell HCT-116.

| | Cell death rate (%) | Combination Index (CI) | | Cell death rate (%) | Combination Index (CI) | | Cell death rate (%) | Combination Index (CI) |
|---|---|---|---|---|---|---|---|---|
| HF 10 nM | 19.41 ± 4.03 | | HF 20 nM | 33.06 ± 3.32 | | HF 40 nM | 59.27 ± 0.41 | |
| ATS 160 μM | 35.89 ± 3.91 | | ATS 320 μM | 48.31 ± 3.61 | | ATS 640 μM | 54.42 ± 2.44 | |
| DAT 160 μM | 36.80 ± 3.33 | | DAT 320 μM | 47.32 ± 3.65 | | DAT 640 μM | 55.57 ± 2.43 | |
| ASU 160 μM | 35.15 ± 3.45 | | ASU 320 μM | 48.31 ± 3.69 | | ASU 640 μM | 53.52 ± 2.46 | |
| ATM 160 μM | 33.17 ± 4.46 | | ATM 320 μM | 46.32 ± 3.45 | | ATM 640 μM | 54.50 ± 2.50 | |
| HF 10 nM + ATS 160 μM | 50.90 ± 1.80 | 0.55 | HF 20 nM + ATS 320 μM | 60.15 ± 2.19 | 0.59 | HF 40 nM + ATS 640 μM | 68.76 ± 0.48 | 0.70 |
| HF 10 nM + DAT 160 μM | 40.90 ± 1.35 | 0.75 | HF 20 nM + DAT 320 μM | 59.12 ± 1.86 | 0.61 | HF 40 nM + DAT 640 μM | 61.24 ± 0.28 | 0.81 |
| HF 10 nM + ASU160 μM | 43.91 ± 1.04 | 0.62 | HF 20 nM + ASU 320 μM | 55.49 ± 2.23 | 0.71 | HF 40 nM + ASU640 μM | 64.71 ± 0.29 | 0.77 |
| HF 10 nM + ATM 160 μM | 46.93 ± 1.15 | 0.59 | HF 20 nM + ATM3 20 μM | 57.42 ± 2.54 | 0.70 | HF 40 nM + ATM 640 μM | 63.75 ± 1.10 | 0.78 |

Breast cancer cell line MCF-7 was seeded on a 96-well plate, with 100 μl of cell suspension in each well. The culture medium was DMEM supplemented with 10% FBS and 2 mM glutamate. 24 hours after cell seeding, the 96-well plate was added with HF, ATS, DAT, ASU, ATM, the combination of HF and ATS, the combination of HF and DAT, the combination of HF and ATM, and the combination of HF and ASU, respectively, and the culture medium of the control group was not added with any drug. 24 hours after adding the compound, the cell survival rate was assessed using the MTT assay, and the combination index (CI) of the combined pharmaceutical of HF and ATS was calculated using the Calcusyn software. The results are shown in Table 2.

TABLE 2

The inhibitory effect of the combined pharmaceutical of HF and ATS on breast cancer cell MCF-7.

| | Cell death rate (%) | Combination Index (CI) | | Cell death rate (%) | Combination Index (CI) | | Cell death rate (%) | Combination Index (CI) |
|---|---|---|---|---|---|---|---|---|
| HF 10 nM | 2.00 ± 1.28 | | HF 20 nM | 3.00 ± 0.55 | | HF 40 nM | 9.10 ± 1.79 | |
| ATS 160 μM | 9.50 ± 0.77 | | ATS 320 μM | 16.50 ± 1.47 | | ATS 640 μM | 33.90 ± 2.00 | |
| DAT 160 μM | 8.81 ± 0.83 | | DAT 320 μM | 16.32 ± 1.65 | | DAT 640 μM | 32.59 ± 2.43 | |
| ASU 160 μM | 9.15 ± 0.92 | | ASU 320 μM | 16.31 ± 1.69 | | ASU 640 μM | 33.57 ± 2.56 | |
| HF 10 nM + ATS 160 μM | 15.80 ± 0.37 | 0.86 | HF 20 nM + ATS 320 μM | 24.30 ± 3.01 | 0.71 | HF 40 nM + ATS 640 μM | 44.70 ± 2.40 | 0.37 |
| HF10 nM + DAT 160 μM | 15.92 ± 0.64 | 0.84 | HF 20 nM + DAT 320 μM | 22.12 ± 1.85 | 0.77 | HF 40 nM + DAT 640 μM | 38.24 ± 0.28 | 0.71 |
| HF 10 nM + ASU 160 μM | 13.92 ± 1.06 | 0.91 | HF 20 nM + ASU 320 μM | 20.49 ± 2.23 | 0.76 | HF 40 nM + ASU 640 μM | 37.71 ± 0.29 | 0.71 |
| HF 10 nM + ATM160 μM | 14.94 ± 1.13 | 0.89 | HF 20 nM + ATM 320 μM | 22.42 ± 2.22 | 0.77 | HF 40 nM + ATM640 μM | 35.75 ± 1.18 | 0.77 |

Liver cancer cell line HepG2 was seeded on a 96-well plate, with 100 μl of cell suspension in each well. The culture medium was DMEM supplemented with 10% FBS and 2 mM glutamate. 24 hours after cell seeding, the 96-well plate was added with HF, ATS, DAT, ASU, ATM, the combination of HF and ATS, the combination of HF and DAT, the combination of HF and ATM, and the combination of HF and ASU, respectively, and the culture medium of the control group was not added with any drug. 24 hours after adding the compound, the cell survival rate was assessed using the MTT assay, and the combination index (CI) of the combined pharmaceutical of HF and ATS was calculated using the Calcusyn software. The results are shown in Table 3.

TABLE 3

The inhibitory effect of the combined pharmaceutical of HF and ATS on liver cancer cell HepG2.

|  | Cell death rate (%) | Combination Index (CI) |  | Cell death rate (%) | Combination Index (CI) |  | Cell death rate (%) | Combination Index (CI) |
|---|---|---|---|---|---|---|---|---|
| HF 10 nM | 0.70 ± 3.11 |  | HF 20 nM | 1.00 ± 2.06 |  | HF 40 nM | 4.00 ± 2.21 |  |
| ATS 160 μM | 0.90 ± 0.95 |  | ATS 320 μM | 1.60 ± 0.08 |  | ATS 640 μM | 6.40 ± 2.71 |  |
| DAT 160 μM | 0.81 ± 0.83 |  | DAT 320 μM | 1.72 ± 0.15 |  | DAT 640 μM | 6.59 ± 2.58 |  |
| ASU 160 μM | 0.95 ± 0.72 |  | ASU 320 μM | 1.86 ± 0.09 |  | ASU 640 μM | 6.57 ± 2.06 |  |
| HF 10 nM + ATS 160 μM | 7.90 ± 4.30 | 0.18 | HF 20 nM + ATS 320 μM | 13.20 ± 5.67 | 0.16 | HF 40 nM + ATS 640 μM | 34.10 ± 4.63 | 0.08 |
| HF10 nM + DAT 160 μM | 2.90 ± 0.31 | 0.45 | HF 20 nM + DAT 320 μM | 4.12 ± 0.81 | 0.41 | HF 40 nM + DAT 640 μM | 11.24 ± 0.28 | 0.22 |
| HF 10 nM + ASU 160 μM | 1.91 ± 0.04 | 0.62 | HF 20 nM + ASU 320 μM | 3.10 ± 0.41 | 0.55 | HF 40 nM + ASU 640 μM | 7.21 ± 0.29 | 0.48 |
| HF 10 nM + ATM 160 μM | 1.94 ± 1.18 | 0.67 | HF 20 nM + ATM 320 μM | 5.42 ± 2.22 | 0.38 | HF 40 nM + ATM 640 μM | 8.75 ± 1.18 | 0.39 |

Gastric cancer cell line MGC803 was seeded on a 96-well plate, with 100 μl of cell suspension in each well. The culture medium was DMEM supplemented with 10% FBS and 2 mM glutamate. 24 hours after cell seeding, the 96-well plate was added with HF, ATS, DAT, ASU, ATM, the combination of HF and ATS, the combination of HF and DAT, the combination of HF and ATM, and the combination of HF and ASU, respectively, and the culture medium of the control group was not added with any drug. 24 hours after adding the compound, the cell survival rate was assessed using the MTT assay, and the combination index (CI) of the combined pharmaceutical of HF and ATS was calculated using the Calcusyn software. The results are shown in Table 4.

TABLE 4

The inhibitory effect of the combined pharmaceutical of HF and ATS on gastric cancer cell MGC803.

|  | Cell death rate (%) | Combination Index (CI) |  | Cell death rate (%) | Combination Index (CI) |  | Cell death rate (%) | Combination Index (CI) |
|---|---|---|---|---|---|---|---|---|
| HF 10 nM | 8.10 ± 2.77 |  | HF 20 nM | 20.00 ± 4.18 |  | HF 40 nM | 29.00 ± 3.31 |  |
| ATS 160 μM | 1.00 ± 3.31 |  | ATS 320 μM | 4.60 ± 5.51 |  | ATS 640 μM | 40.00 ± 3.18 |  |
| DAT 160 μM | 1.81 ± 0.83 |  | DAT 320 μM | 5.32 ± 1.65 |  | DAT 640 μM | 42.59 ± 2.43 |  |
| ASU 160 μM | 1.15 ± 0.92 |  | ASU 320 μM | 5.31 ± 1.69 |  | ASU 640 μM | 43.57 ± 2.56 |  |
| HF 10 nM + | 23.78 ± 4.73 | 0.42 | HF 20 nM + | 34.54 ± 4.92 | 0.46 | HF 40 nM + ATS | 64.70 ± 5.46 | 0.20 |

TABLE 4-continued

The inhibitory effect of the combined pharmaceutical of HF and ATS on gastric cancer cell MGC803.

| | Cell death rate (%) | Combination Index (CI) | | Cell death rate (%) | Combination Index (CI) | | Cell death rate (%) | Combination Index (CI) |
|---|---|---|---|---|---|---|---|---|
| ATS 160 μM | | | ATS 320 μM | | | 640 μM | | |
| HF10 nM + DAT 160 μM | 20.90 ± 1.33 | 0.75 | HF 20 nM + DAT 320 μM | 29.16 ± 3.56 | 0.52 | HF 40 nM + DAT 640 μM | 61.24 ± 0.28 | 0.38 |
| HF 10 nM + ASU 160 μM | 23.21 ± 3.14 | 0.62 | HF 20 nM + ASU 320 μM | 27.32 ± 2.26 | 0.59 | HF 40 nM + ASU 640 μM | 64.71 ± 3.29 | 0.21 |
| HF 10 nM + ATM 160 μM | 20.94 ± 1.55 | 0.79 | HF 20 nM + ATM 320 μM | 28.42 ± 2.25 | 0.57 | HF 40 nM + ATM 640 μM | 60.75 ± 1.16 | 0.41 |

Melanoma cell line A375 was seeded on a 96-well plate, with 100 μl of cell suspension in each well. The culture medium was DMEM supplemented with 10% FBS and 2 mM glutamate. 24 hours after cell seeding, the 96-well plate was added with HF, ATS, DAT, ASU, ATM, the combination of HF and ATS, the combination of HF and DAT, the combination of HF and ATM, and the combination of HF and ASU, respectively, and the culture medium of the control group was not added with any drug. 24 hours after adding the compound, the cell survival rate was assessed using the MTT assay, and the combination index (CI) of the combined pharmaceutical of HF and ATS was calculated using the Calcusyn software. The results are shown in Table 5.

TABLE 5

The inhibitory effect of the combined pharmaceutical of HF and ATS on melanoma cell A375.

| | Cell death rate (%) | Combination Index (CI) | | Cell death rate (%) | Combination Index (CI) | | Cell death rate (%) | Combination Index (CI) |
|---|---|---|---|---|---|---|---|---|
| HF 10 nM | 5.70 ± 5.44 | | HF 20 nM | 17.70 ± 2.82 | | HF 40 nM | 35.70 ± 4.76 | |
| ATS 160 μM | 16.50 ± 4.30 | | ATS 320 μM | 26.30 ± 1.33 | | ATS 640 μM | 46.50 ± 3.57 | |
| DAT 160 μM | 16.81 ± 5.83 | | DAT 320 μM | 26.35 ± 1.64 | | DAT 640 μM | 42.55 ± 4.42 | |
| ASU 160 μM | 16.15 ± 4.90 | | ASU 320 μM | 25.38 ± 1.65 | | ASU 640 μM | 47.59 ± 3.93 | |
| HF 10 nM + ATS 160 μM | 33.70 ± 4.75 | 0.42 | HF 20 nM + ATS 320 μM | 54.40 ± 4.33 | 0.21 | HF 40 nM + ATS 640 μM | 66.60 ± 0.94 | 0.20 |
| HF10 nM + DAT 160 μM | 27.90 ± 1.35 | 0.74 | HF 20 nM + DAT 320 μM | 47.13 ± 1.86 | 0.46 | HF 40 nM + DAT 640 μM | 51.24 ± 0.28 | 0.31 |
| HF 10 nM + ASU 160 μM | 23.95 ± 1.23 | 0.62 | HF 20 nM + ASU 320 μM | 35.49 ± 2.23 | 0.80 | HF 40 nM + ASU640 μM | 44.71 ± 0.29 | 0.49 |
| HF 10 nM + ATM 160 μM | 24.95 ± 1.08 | 0.89 | HF 20 nM + ATM 320 μM | 42.51 ± 1.20 | 0.57 | HF 40 nM + ATM 640 μM | 45.75 ± 0.18 | 0.42 |

In reference to the method in the Soriano A F et al., Synergistic effects of new chemopreventive agents and conventional cytotoxic agents against human lung cancer cell lines, Cancer Res, 1999, 59 (24): 6178-6184, the inhibitory effect investigation on colon cancer cell HCT-116 shows that the CIs of the combination of HF and ATS were was 0.55-0.7. Such synergistic effect exhibited a decreasing trend with the increase of the pharmaceutical concentration, regarded as moderate synergistic effect. The CIs of the combination of HF and DAT were 0.75, 0.61, and 0.81 respectively, regarded as moderate and low synergistic effect. The CIs of the combination of HF and ASU were 0.62-0.77. Such synergistic effect exhibited a decreasing trend with the increase of the pharmaceutical concentration, regarded as moderate synergistic effect. The CIs of the combination of HF and ATM were 0.50-0.78, regarded as moderate synergistic effect. The inhibitory effect investigation on breast cancer cell MCF-7 shows that the CIs of the combination of HF and ATS were 0.37-0.86. Such synergistic effect exhibited an increasing trend with the increase of the pharmaceutical concentration. The CIs of the combination of HF and DAT were 0.84, 0.77, and 0.71 respectively, regarded as low synergistic effect. The CIs of the combination of HF and ASU were 0.91, 0.76, and 0.71, respectively, having synergistic effect. The CIs of the combination of HF and ATM were 0.88, 0.77, and 0.77 respectively, having moderate synergistic effect. The inhibitory effect investigation on liver cancer cell HepG2 shows that the CIs of combination of HF and ATS were 0.08-0.18. Such synergistic effect exhibited an increasing trend with the increase of the pharmaceutical concentration. The combined pharmaceutical of HF and artemisinin can be regarded as strong synergistic effect. The CIs of the combination of HF and DAT were 0.45-0.22, regarded as high and strong synergistic effect. The CIs of the combination of HF and ASU were 0.62, 0.55, and 0.48, respectively, regarded as high synergy. The CIs of the combination of HF and ATM were 0.67, 0.38, and 0.39, respectively, having moderate synergistic effect. The inhibitory effect investigation on gastric cancer cell MGC803 shows that the CIs of the combination of HF and ATS were 0.20-0.42. Such synergistic effect exhibited an increasing trend with the increase of the pharmaceutical concentration. The combined pharmaceutical of HF and ATS can be regarded as high synergistic effect. The CIs of the combination of HF and DAT were 0.75-0.38. Such synergistic effect exhibited an increasing trend with the increase of the pharmaceutical concentration, regarded as moderate and high synergistic effect. The CIs of the combination of HF and ASU 0.62-0.21, the synergistic effect of which exhibited an increasing trend with the increase of the pharmaceutical concentration, regarded as moderate and high synergistic effect, and can be understood as high and strong synergy. The CIs of the combination of HF and ATM were 0.79, 0.57, and 0.41, respectively, regarded as moderate synergistic effect. The inhibitory effect investigation on melanoma cell A375 shows that the CIs of the combination of HF and ATS were 0.20-0.42. Such synergistic effect exhibited an increasing trend with the increase of the pharmaceutical concentration. The combined pharmaceutical of HF and ATS can be regarded as high synergistic effect. The CIs of the combination of HF and DAT were 0.74-0.31, the synergistic effect of which exhibited an increasing trend with the increase of the pharmaceutical concentration, regarded as moderate and low synergistic effect. The CIs of the combination of HF and ASU were 0.62, 0.80, and 0.21, respectively, regarded as moderate and low synergistic effect. The CIs of the combination of HF and ATM were 0.89, 0.57, and 0.42, respectively, having synergistic effect.

It can be seen from the aforementioned inhibitory results of the combined pharmaceutical of HF and an *Artemisia annua* sesquiterpene lactone compound on the 5 cancer cell lines, that the activity of the combined pharmaceutical of HF and ATS and derivatives thereof is significantly higher than that of the HF alone and *Artemisia annua* sesquiterpene lactone compounds alone. Wherein, the activity of the combined pharmaceutical of ATS and HF is the most significant.

Figure 2:
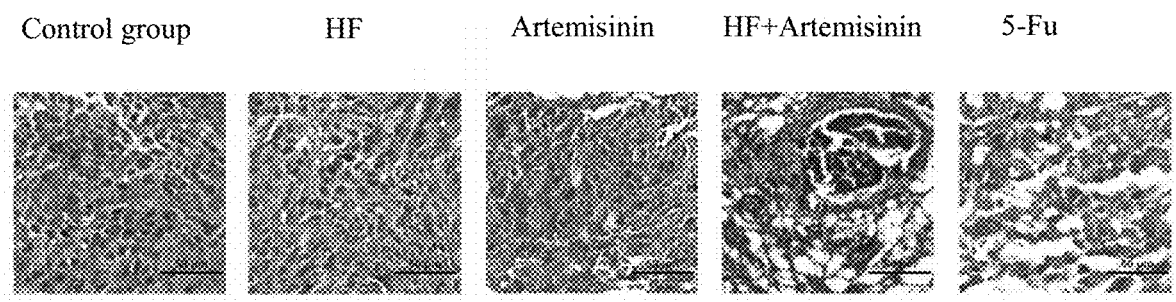
FIG. 2 illustrates the HE staining of the animal sections.
Figure 3:
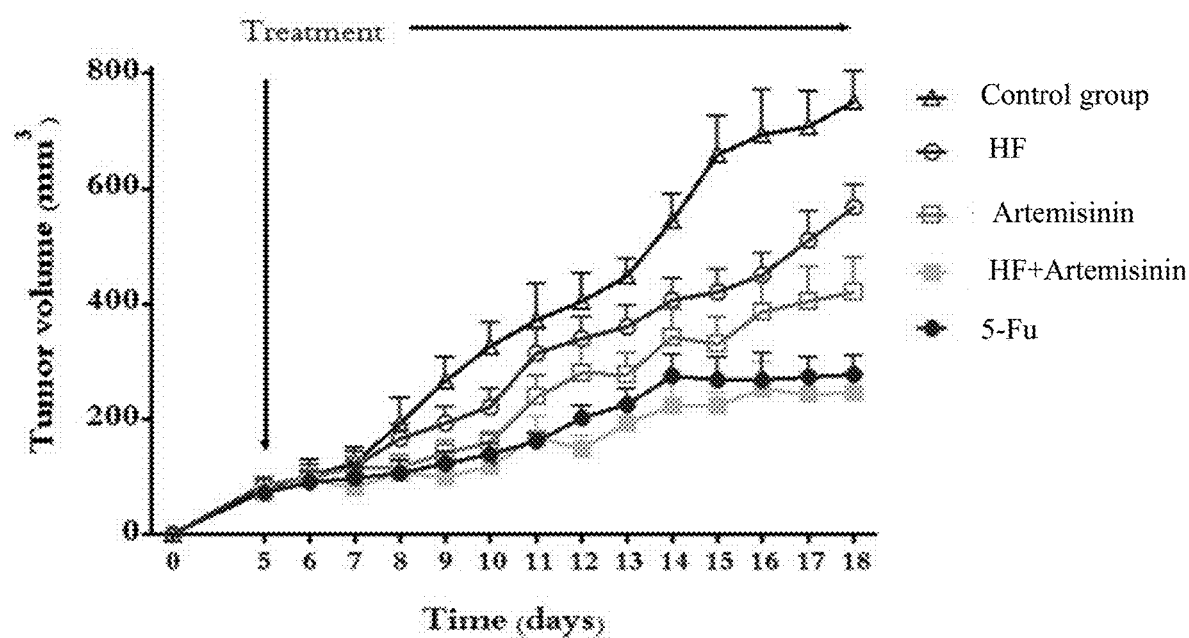
FIG. 3 illustrates the comparison of the activity between the combined pharmaceutical of ATS and HF, and the single pharmaceutical of either ATS or HF.

Embodiment 2: In Vivo Investigation on the Inhibitory Effect of the Combinational Pharmaceutical of HF and ATS on Colon Cancer The combination of ATS and HF, ATS alone and HF alone were subjected to animal experiments, with 5-FU as a control drug. The colon cancer cells HCT-116 were inoculated under the skin of female nude mice. Each mouse was inoculated with $1\times10^6$ cells. Pharmaceuticals were administrated after 5 days when the tumor volume reached about 100 mm$^3$. The dose of HF was 5 μg/kg, the dose of ATS was 50 mg/kg, the dose of the combined pharmaceutical of HF and ATS was the sum of the doses of HF and ATS, and the dose of 5-FU was 10 mg/kg. Each group was administered intraperitoneally once a day. After 15 days, the tumors were excised (FIG. 1), and were subjected to pathological biopsy examination (FIG. 2). It was found that the combination of HF and ATS had significant synergistic effect, which was significantly better than ATS or HF alone (FIG. 3). Moreover, the activity of the combination of HF and ATS was higher than that of 5-FU.

The combination of HF and ATS with different mass ratios were subjected to animal experiments according to the aforementioned method, wherein the first group was administered with 100 μg/kg HF and 20 mg/kg ATS, and the second group was administered with 2 μg/kg HF and 100 mg/kg ATS. Results show that the activities of the combinations of ATS and HF with different mass ratios were comparable with the efficacy of 5-FU. The efficacies of the combinations of ATS and HF with different mass ratios were still higher than that of ATS or HF alone.

In summary, the combination of ATS and HF has significant therapeutic effect on colon cancer. The activity of the combination of ATS and HF is comparable with the efficacy of 5-FU. Within the range of 0.1:20 to 0.002:100 of HF and ATS (the mass ratio of HF:ATS is $1:2\times10^2$-$5\times10^5$), the HF and ATS has good synergistic effect, and can be used as an effective combined pharmaceutical.

The invention claimed is:

1. A combined pharmaceutical composition comprising halofuginone (HF) and an *Artemisia annua* sesquiterpene lactone compound, wherein active ingredients of said composition consist of HF and the *Artemisia annua* sesquiterpene lactone compound is artemisinin (ATS).

2. A method of treating colon cancer, the method comprising administering the pharmaceutical composition of claim 1 to a subject.

3. A method of treating breast cancer, the method comprising administering the pharmaceutical composition of claim 1 to a subject.

4. A method of treating liver cancer, the method comprising administering the pharmaceutical composition of claim 1 to a subject.

5. A method of treating gastric cancer, the method comprising administering the pharmaceutical composition of claim 1 to a subject.

6. A method of treating melanoma, the method comprising administering the pharmaceutical composition of claim 1 to a subject.

* * * * *